United States Patent
Liu et al.

(10) Patent No.: US 10,561,695 B2
(45) Date of Patent: Feb. 18, 2020

(54) COMPOSITION HAVING FUNCTIONS OF IMPROVING KIDNEY YANG, ENHANCING IMMUNITY AND RELIEVING FATIGUE, METHOD FOR PRODUCING THE SAME AND USE THEREOF

(71) Applicant: INFINITUS (CHINA) COMPANY LTD., Jiangmen, Guangdong (CN)

(72) Inventors: Shuo Liu, Guangdong (CN); Wenzhi Li, Guangdong (CN); Siyao Ma, Guangdong (CN)

(73) Assignee: INFINITUS (CHINA) COMPANY LTD., Jiangmen, Guangdong (CN)

( * ) Notice: Subject to any disclaimer, the term of this patent is extended or adjusted under 35 U.S.C. 154(b) by 0 days.

(21) Appl. No.: 16/236,513

(22) Filed: Dec. 30, 2018

(65) Prior Publication Data

US 2019/0365841 A1    Dec. 5, 2019

(30) Foreign Application Priority Data

Jun. 4, 2018   (CN) .......................... 2018 1 0562917

(51) Int. Cl.

| A61K 36/481 | (2006.01) |
| A61K 36/64 | (2006.01) |
| A61K 36/46 | (2006.01) |
| A61P 43/00 | (2006.01) |
| A61K 36/815 | (2006.01) |
| A61K 36/88 | (2006.01) |
| A61P 37/00 | (2006.01) |
| A61K 36/746 | (2006.01) |

(52) U.S. Cl.
CPC ............ *A61K 36/481* (2013.01); *A61K 36/46* (2013.01); *A61K 36/64* (2013.01); *A61K 36/746* (2013.01); *A61K 36/815* (2013.01); *A61K 36/88* (2013.01); *A61P 37/00* (2018.01); *A61P 43/00* (2018.01)

(58) Field of Classification Search
None
See application file for complete search history.

(56) References Cited

FOREIGN PATENT DOCUMENTS

| CN | 1958039 A | * | 5/2007 |
| CN | 106421649 A | * | 2/2017 |

* cited by examiner

*Primary Examiner* — Susan Hoffman
(74) *Attorney, Agent, or Firm* — Yue (Robert) Xu; Apex Attorneys at Law, LLP

(57) ABSTRACT

The present disclosure relates to the field of healthcare foods. Disclosed is a composition having functions of improving kidney yang, enhancing immunity and relieving fatigue, which is an aqueous extract of *Astragalie radix, Rehmanniae radix, Eucommiae cortex, Morindae officinalis radix, Lycii fructus* and *Polygonati rhizoma*. By using six traditional Chinese herb medicines, *Astragalie radix, Rehmanniae radix, Eucommiae cortex, Morindae officinalis radix, Lycii fructus* and *Polygonati rhizoma* for decoction extraction, a composition having functions of improving kidney yang, enhancing immunity and relieving fatigue is obtained. Through synergetic function of each traditional Chinese herb medicine, the composition achieves a better effect comparing with similar products. In addition, the species of traditional Chinese medicine in the composition is relatively fewer, lowering the potential safety hazard, and the method is simple and the cost is low.

1 Claim, No Drawings

COMPOSITION HAVING FUNCTIONS OF IMPROVING KIDNEY YANG, ENHANCING IMMUNITY AND RELIEVING FATIGUE, METHOD FOR PRODUCING THE SAME AND USE THEREOF

CROSS REFERENCE TO RELATED APPLICATIONS

This application claims the priority of Chinese Patent Application No. 201810562917.9, filed on Jun. 4, 2018, and the disclosures of which are hereby incorporated by reference.

FIELD

The present disclosure relates to the field of healthcare food technology, specifically to a composition having functions of ameliorating Kidney-Yang Deficiency Syndrome, enhancing immunity and relieving fatigue, method for producing the same and use thereof.

BACKGROUND

In the high-strength and fast-paced work and live now, due to factors such as psychological stress, physical fatigue, negative and pessimism, unbalanced diet, lack of exercise, excessive antibacterial, and so on, more and more people are suffering from a sub-healthy state: decreased immunity, fatigue, and Kidney-Yang Deficiency Syndrome, which brings many influences on daily life and work.

In modern medicine, it is believed that a network is formed between the neuroendocrine system and the immune system, and many researches indicate that hypothalamus is the hub of the network. Kidney-Yang Deficiency Syndrome is due to the abnormal expression of the genes mediates the network balance, which causes the functional imbalance of neuroendocrine-immune network. Large dosage of exterior glucocorticoid can cause a "depletion" phenomenon in animals and a series of "weak" symptoms, which are similar to "yang deficiency" in Chinese medicine. Studies found that when Kidney-Yang Deficiency Syndrome exists, hypothalamic-pituitary-target gland (adrenal gland, thyroid gland, and gonad) axis showed dysfunction at different links and different levels, and these dysfunctions of the axis are relatively specific indicators reflecting the Kidney-Yang Deficiency Syndrome.

At present, there are many Chinese medicine products that enhance immunity and improve kidney yang, but these products usually have twenty or more Chinese medicine components, which on one hand brings potential medication hazard to consumers, on the other hand enhances the complexity and cost of production; in addition, a multiple of Chinese medicine components do not give these products more excellent efficacies and functions.

SUMMARY

In view of this, an object of the present disclosure is to provide a composition having functions of improving kidney yang, enhancing immunity and relieving fatigue, and the composition achieves an excellent efficacy of improving kidney yang, enhancing immunity and relieving fatigue by using relatively less traditional Chinese herb medicine components.

In order to achieve the goal of the present disclosure, the present disclosure provides the following technical solutions.

A composition having functions of improving kidney yang, enhancing immunity and relieving fatigue, which is an extract obtained by extracting *Astragalie radix*, *Rehmanniae radix*, *Eucommiae cortex*, *Morindae officinalis radix*, *Lycii fructus* and *Polygonati rhizoma* with water.

In order to solve the deficiencies of similar products, such as relatively multiple kinds of medicines and poor efficacy, in the present disclosure, six suitable traditional Chinese herb medicines are used for extraction with water to prepare a composition having functions of improving kidney yang, enhancing immunity and relieving fatigue. The active ingredients of each traditional Chinese herb medicine have synergetic functions and perform excellent efficacies.

As preferred, the weight ratio of *Astragalie radix*, *Rehmanniae radix*, *Eucommiae cortex*, *Morindae officinalis radix*, *Lycii fructus* and *Polygonati rhizoma* is (3 to 8):(2 to 6):(1 to 4):(0.5 to 2):(0.5 to 1):(0.5 to 1); and more preferably, the weight ratio of *Astragalie radix*, *Rehmanniae radix*, *Eucommiae cortex*, *Morindae officinalis radix*, *Lycii fructus* and *Polygonati rhizoma* is 4:3:2:1:0.75:0.75. In the specific embodiments of the present disclosure, the composition is prepared from 40 parts by weight of *Astragalie radix*, 30 parts by weight of *Rehmanniae radix*, 20 parts by weight of *Eucommiae cortex*, 10 parts by weight of *Morindae officinalis radix*, 7.5 parts by weight of *Lycii fructus* and 7.5 parts by weight of *Polygonati rhizoma*. The term "parts by weight" in the present disclosure may be in any forms of mass unit, and may be adjusted in equal proportions.

In the animal model test, the composition of the present disclosure shows functions on enhancing immunity: obviously increasing the thymus coefficient of mouse with low immunity, enhancing the proliferation ability of the lymphocyte, increasing the content of antibody of serum hemolysin of mouse with low immunity, increasing the phagocytic index of mouse with low immunity, enhancing the activity of NK cells, increasing the killing rate of the NK cells. In addition, the composition of the present disclosure has functions of relieving fatigue and ameliorating animals with Kidney-Yang Deficiency Syndrome (animal model): significantly increasing the thymus coefficient, hypophysis coefficient and thyroid gland coefficient of animal with Kidney-Yang Deficiency Syndrome, increasing the serum corticotropin releasing hormone (CRH) and cortisol (Cor) levels in rats with Kidney-Yang Deficiency Syndrome, increasing the serum thyrotropin-releasing hormone (TRH), triiodothyronine (T3) and tetraiodothyronine (T4) levels in rats with Kidney-Yang Deficiency Syndrome, and increasing the follicle stimulating hormone (FSH) and testosterone (T) levels in rats with Kidney-Yang Deficiency Syndrome.

In addition, in the evaluation test among the crowd, the composition of the present disclosure has excellent effects and short onset time on immunity/fatigue (poor immunity, dizziness, easy to be fatigue/weak, sleepiness and lack of concentration) and Kidney-Yang Deficiency Syndrome (waist and knees aching and limping, afraid of chill and cold, limbs chilling, frequent nocturia and loss of libido).

On the base of the excellent effects above, the present disclosure provides a use of the composition in preparing drugs and/or healthcare foods having one, or more than one functions of improving kidney yang, improving immunity and relieving fatigue. Therein, the heath care foods may be in the form of oral liquid, tablet, capsule, pill or granule.

The present disclosure further provides the method for producing the composition, comprising:

mixing *Astragalie radix, Rehmanniae radix, Eucommiae cortex, Morindae officinalis radix, Lycii fructus* and *Polygonati rhizoma*, subjecting the mixture to decoction extraction, concentrating the resultant extract to a extractum and filtrating, centrifuging the resultant filtrate to remove precipitations, and obtaining the composition.

Therein, as preferred, decoction extraction is performed by adding water 10 to 12 times the weight of total starting materials and extracting in boiling water for 60 to 90 min.

Preferably, the decoction extraction is performed twice.

In the specific embodiments of the present disclosure, the method comprises, mixing *Astragalie radix, Rehmanniae radix, Eucommiae cortex, Morindae officinalis radix, Lycii fructus* and *Polygonati rhizoma*, adding distilled water 12 times the weight of starting materials, boiling and extracting for 90 min, and collecting the filtrate upon filtration; adding distilled water 10 times the weight of filter cake, boiling and extracting for 60 min; combing the two filtrates, and subjecting the resultant filtrate to 80-mesh filtration; performing vacuum concentration under condition of −0.05 MPa at 70° C. to obtain the extractum, adding purified water and a sweetener to the extractum, mixing under stirring for 30 min, centrifuging to remove precipitations, and sterilizing at a high temperature to obtain the composition.

It can be concluded from the technical solution that in the present disclosure, six traditional Chinese herb medicines, *Astragalie radix, Rehmanniae radix, Eucommiae cortex, Morindae officinalis radix, Lycii fructus* and *Polygonati rhizoma*, are used as the components to produce a composition having functions of improving kidney yang, enhancing immunity and relieving fatigue by method of decoction extraction. Through the synergistic function of each traditional Chinese herb medicine, the product has a better effect than similar products. In addition, the species of traditional Chinese herb medicine used in the present disclosure are relatively fewer, which lower the potential safety risks for consumers. The preparation method is simple and the cost is low.

DETAILED DESCRIPTION

The present disclosure provides a composition having functions of improving kidney yang, enhancing immunity and relieving fatigue, method for producing the same and use thereof. One of ordinary skill in the art can learn from the contents of this document and appropriately improve the process parameters. It should be noted that all such alternatives and modifications are obvious to one of ordinary skill in the art and are considered to be included in the present disclosure. The composition of the present disclosure, a method for producing the same and the use thereof have been described by way of examples. It will be apparent that one of ordinary skill in the art will be able to implement and practice the techniques of the present disclosure without departing from the spirit and scope of the disclosure.

In the specific embodiments of the present disclosure, there are some comparative experiments, except for the desired differences, the environment and raw materials of each experimental group are the same.

In the present disclosure, the tests of enhancing immunity and relieving fatigue are performed according to the standard in *Technical specification for healthcare food inspection and evaluation*, which is a national specification for healthcare food declaration.

A composition having functions of improving kidney yang, enhancing immunity and relieving fatigue, method for producing the same and use thereof provided by the present disclosure will be further illustrated hereinafter.

Example 1: Preparation of Composition of the Present Disclosure

Starting materials: 40 parts by weight of *Astragalie radix*, 30 parts by weight of *Rehmanniae radix*, 20 parts by weight of *Eucommiae cortex*, 10 parts by weight of *Morindae officinalis radix*, 7.5 parts by weight of *Lycii fructus* and 7.5 parts by weight of *Polygonati rhizoma* (the weight ratio was 4:3:2:1:0.75:0.75) were mixed, and distilled water which was 12 times the weight of the starting materials was added. The mixture was boiled and extracted for 90 min, and the filtrate was collected upon filtration. Distilled water which was 10 times the weight of filter cake was added, the mixture was boiled and extracted for 60 min. The two filtrates were combined, and subjected to 80-mesh filtration. The resultant was subjected to vacuum concentration under −0.05 MPa at 70° C. to give an extractum, of which the content of soluble solid was 25%. The extractum was refrigerated at 0° C. for 12 h, was and then subjected to 80-mesh filtration. Purified water and a small amount of sucralose were added for seasoning, and the mixture was stirred for 30 min to give a stock solution with a content of soluble solid of 11%. The precipitations were removed by centrifuge at a speed of 15,000 rpm. The resultant was subjected to high temperature sterilization at 121° C. for 30 min to give the composition having functions of improving kidney yang/enhancing immunity/relieving fatigue.

Example 2: Animal Model Test

1. Test Drug

The composition obtained in Example 1 of the present disclosure.

2. Dosage Design

In experiments for enhancing immunity and relieving fatigue: the experimental animals were randomly divided into control group, model control group, and three dosage groups of the composition of Example 1, including low dosage group, middle dosage group and high dosage group (respectively corresponding to 5 times, 10 times and 20 times of the recommended amount for human). There were 10 animals in each group.

In experiments for ameliorating Kidney-Yang Deficiency Syndrome: the experimental animals were randomly divided into control group, model control group, and three dosage groups of the composition of Example 1, including low dosage group, middle dosage group and high dosage group (respectively corresponding to 2.5 times, 5 times and 10 times of the recommended amount for human). There were 10 animals in each group.

3. Experimental Animals

KM mice, SPF grade, certificate No. SCXK (Yue) 2008-0020 Yue Supervisory Certificate 2008A003, were purchased from Experimental Animal Center of Guangzhou University of Traditional Chinese Medicine. SD rats, SPF grade, certificate No. SCXK (Yue) 2008-0002 Yue Supervisory Certificate 2008A020, were purchased from Guangdong Medical Laboratory Animal Center.

4. Experiment for Enhancing Immunity (1) Effects on Weight of Immune Organs

70 MK mice, half the male and half the female, weight 13 to 15 g, were used in the experiment. The mice were randomly divided into normal control group, model control group, and three dosage groups of the composition of Example 1, including low dosage group, middle dosage group and high dosage group. The mice were administered by intragastric gavage once per day according to their body weights and the administration lasted for 10 days. The normal control group was administered with equal volume of distilled water. Except for the normal control group, the other groups were subjected to subcutaneous injection with cyclophosphamide of 50 mg/kg/day from the 7th day, and lasted for 4 days. 1 hour after the last administration, the mice were sacrificed by cervical dislocation. The thymuses and spleens were taken out and accurately weighed, and the organ coefficients were calculated.

$$\text{Organ coefficient} = \frac{\text{weight of the organ (mg)}}{\text{body weight (g)}} \times 100\%$$

TABLE 1

Effects on weights of the immune organs ($\bar{x} \pm s$)

| Group | Dosage (ml/kg) | N (animal number) | Organ Coefficient | |
|---|---|---|---|---|
| | | | Thymus Coefficient | Spleen Coefficient |
| Normal Control Group | — | 10 | 3.281 ± 1.216 | 2.646 ± 0.977 |
| Model Control Group | — | 10 | 1.235 ± 0.333▲▲ | 1.647 ± 0.205▲▲ |
| Low Dosage Group | 1.67 | 10 | 1.268 ± 0.270 | 1.650 ± 0.312 |
| Middle Dosage Group | 3.33 | 10 | 1.424 ± 0.313 | 1.834 ± 0.324 |
| High Dosage Group | 6.67 | 10 | 1.780 ± 0.316* | 1.724 ± 0.358 |

Comment: ▲ indicating that comparing with the normal control group, P<0.05; ▲▲ indicating that comparing with the normal control group, P<0.01; * indicating that comparing with the normal control group, P<0.05; ** indicating that comparing with the normal control group, P<0.01.

Results of Table 1 showed that the composition in high dosage obviously increased the thymus coefficient (P<0.05) of mice with low immunity.

(2) Test of Cellular Immune Function

KM mice were used in the experiment, half the male and half the female, weight 18 to 22 g. The mice were randomly divided into normal control group and three dosage groups of the composition of Example 1, including low dosage group, middle dosage group and high dosage group. There were 10 animals in each group. The mice were administered by intragastric gavage once per day according to their body weights and the administration lasted for 10 days. The normal control group was administered with equal volume of distilled water. 24 h after the last administration, the animals were sacrificed, and a suspension of spleen cells was prepared under aseptic conditions.

1) Preparation of the suspension of spleen cells: mice were sacrificed by cervical dislocation, the mice were immersed in 75% ethanol for about 1 min; the spleen was taken out on a super-clean bench and disposed in RPMI 1640 culture medium without serum. The spleen was homogenized to single cells with a 100-mesh stainless steel mesh and centrifuged at 1000 rpm for 5 min. The supernatant was discarded and the cell precipitation was gently knocked for loose. 0.4 mL of double distilled water was added to the cells and gently shaken for 30 s to break the red blood cells under low osmotic pressure. Then 0.4 mL of double-concentration physiological saline (1.8%) was added so that the solution recovered isosmotic. The cells suspension was subjected to centrifugation at 1000 rpm for 5 min, and washed twice with 1640 culture medium without serum. The cell precipitation was re-suspended in 1640 culture medium containing 10/o of calf serum and counted under a microscope. The cell concentration was adjusted to $5 \times 10^6$/mL, i.e., the spleen cells for use.

2) Lymphocyte proliferation test: 100 L of the prepared spleen cell suspension and 100 μL of ConA (final concentration 3.75 μg/ml) were respectively added to each well of a 96-well plastic plate. In the control wells, 100 μl of RPMI-1640 culture medium was added. There were 2 experiment wells and 2 control wells for each of the mice. The plate was disposed in an incubator with 5% $CO_2$ at 37° C. for 66 h. The plate was taken out, and 10 μL of CCK-8 was added to each well, and then the plate was cultured for 2.5 h. After the completion of culture, the optical density was measured with an enzyme-linked analyzer at 490 nm wavelength. The lymphocyte proliferation ability is calculated by optical density of the ConA-added well minus the optical density of the well without ConA. Simulation index=OD value of the experiment group/OD value of the control group.

TABLE 2

Effects on lymphocyte proliferation ($\bar{x} \pm s$)

| Group | Dosage (mL/kg) | N (animal number) | Simulation index |
|---|---|---|---|
| Normal Control Group | — | 10 | 1.08 ± 0.04 |
| Low Dosage Group | 1.67 | 10 | 1.12 ± 0.09 |
| Middle Dosage Group | 3.33 | 10 | 1.20 ± 0.08* |
| High Dosage Group | 6.67 | 10 | 1.21 ± 0.17* |

Comment: * indicating that comparing with the normal control group, P<0.05; ** indicating that comparing with the normal control group, P<0.01.

The results of Table 2 showed that the high dosage group of the composition in the Example 1 significantly improved the lymphocyte proliferation ability (p<0.05).

(3) Test of Monocyte-Macrophage Functions

KM mice were used, half male and half female, weight 18 to 22 g. The mice were randomly divided into normal control group, model control group, and three dosage groups of the composition of Example 1, including low dosage group, middle dosage group and high dosage group. There were 10 animals in each group. The mice were administered by intragastric gavage once per day according to their body weights and the administration lasted for 10 days. The normal control group was administered with equal volume of distilled water. From the $8^{th}$ day, the mice were subcutaneous injected with cyclophosphamide in an amount of 40 mg/kg/day for 3 days. 24 h after the last administration, diluted Zhonghua ink (50%) was intravenous injected in an amount of 0.1 mL/10 g body weight. 30 s and 6 min after injecting the ink, 0.025 mL of blood was collected from the mouse orbit with a micropipettor, and immediately added to 2 mL of 0.1% $NaCO_3$ (sodium carbonate) solution. The blood adhered on the pipette tip was fully washed out by sucking the solution up and down several times. After blood collection, 0.025 mL of normal mouse blood dissolved in 2 mL of 0.1% NaCO₃ (sodium carbonate) solution was used to set zero point for calibration. Colorimetry was carried out on a spectrophotometer at 675 nm. The phagocytic index K and phagocytic coefficient (corrected phagocytic coefficient) a was calculated according to the following formula. The results were recorded and subjected to statistical analysis. The results were shown in Table 3.

$$K = \frac{lgC_1 - lgC_2}{T_2 - T_1}, \alpha = \frac{W}{WLS} \times \sqrt[3]{K}$$

In the formula, C is the content of carbon particles in blood; T is the time (min); W is the body weight (g); and WLS is the total weight of liver and spleen (g).

TABLE 3

Results of carbon clearance test ($\bar{x} \pm s$)

| Group | Dosage (ml/kg) | N (animal number) | Phagocyte Index K | Phagocytic Coefficient α |
|---|---|---|---|---|
| Blank Group | — | 10 | 0.035 ± 0.016 | 4.85 ± 1.09 |
| Model Group | — | 10 | 0.013 ± 0.007▲▲ | 4.69 ± 1.01 |
| Low Dosage Group | 1.67 | 10 | 0.018 ± 0.013 | 4.99 ± 1.46 |
| Middle Dosage Group | 3.33 | 10 | 0.025 ± 0.010* | 4.16 ± 0.99 |
| High Dosage Group | 6.67 | 10 | 0.025 ± 0.008* | 3.86 ± 0.79 |

Comment: ▲ indicating that comparing with the normal control group, P<0.05; ▲ð indicating that comparing with the normal control group, P<0.01; * indicating that comparing with the normal control group, P<0.05; ** indicating that comparing with the normal control group, P<0.01.

Results of Table 3 showed that the high dosage group of Example 1 improved phagocyte index K (p<0.05).

(4) Test of Humoral Immunity Function (Test of the Content of Serum Hemolysin Antibody)

70 mice were used, half male and half female, weight 18 to 22 g. The mice were randomly divided into normal control group, model control group, 0712-02 control group, and three dosage groups of the composition of Example 1, including low dosage group, middle dosage group and high dosage group. There were 10 animals in each group. The mice were administered by intragastric gavage according to their body weights and the administration lasted for 10 days. From the 1$^{st}$ day of the experiment, except for the normal control group, the other groups were subjected to subcutaneous injection with cyclophosphamide of 40 mg/kg/day for 3 days. On the 4$^{th}$ day of the experiment, 0.2 mL of sheep red blood cells was peritoneal injected into animals of each group. 1 h after the last administration, blood was collected from the orbit of the animal, and the serum was separated out.

Preparation of sheep red blood cell (SRBC): two volume Alsever solution and one volume sheep red blood cells were mixed well and stored in a refrigerator at 4° C. for use. Before use, the stored sheep red blood cells were washed with physiological saline for 3 times (2000 rpm, 5 min). The supernatant was discarded. The cells were diluted with physiological saline in a ratio of 3:5.

Preparation of complement: 15 guinea pigs were subjected to hemospasia from heart. The serum was separated by centrifugation and stored at −20° C. Before use, the serum was diluted with physiological saline in a ratio of 1:10.

Test of hemolysin: the serum from the mice was diluted 500 times with physiological saline. 1 mL of the diluted (1:500) experimental mouse serum, 1 mL of the diluted (1:10) complement serum and 0.5 mL of diluted SRBC were respectively added to a sample tube and mixed well. In a blank tube, the same amount of complement and SRBC, and 1 mL of physiological saline were added. Thereafter, all tubes were put in a water bath at 37° C. for 10 min, and then the tubes were put on ice to stop the reaction. After a centrifugation at 2000 rpm for 10 min, supernatant was collected. The blank tube was used to calibrate zero point, and OD value of each tube was measured at 540 nm with a visible light spectrophotometer. The results were recorded and subjected to statistical analysis. The results were shown in Table 4.

TABLE 4

Effects on content of serum hemolysin antibody ($\bar{x} \pm s$)

| Group | Dosage (ml/kg) | N (animal number) | OD Value |
|---|---|---|---|
| Normal Control Group | — | 10 | 1.069 ± 0.347 |
| Model Control Group | — | 10 | 0.184 ± 0.042▲▲ |
| Low Dosage Group | 1.67 | 10 | 0.234 ± 0.085 |
| Middle Dosage Group | 3.33 | 10 | 0.248 ± 0.077* |
| High Dosage Group | 6.67 | 10 | 0.281 ± 0.107* |

Comment: ▲ indicating that comparing with the normal control group, P<0.05; ▲▲ indicating that comparing with the normal control group, P<0.01; * indicating that comparing with the normal control group, P<0.05; ** indicating that comparing with the normal control group, P<0.01.

Results of Table 4 showed that the high dosage group of Example 1 significantly increased the content of serum hemolysin antibody (p<0.05).

(5) Test of NK Cell Activity

KM mice were used in the experiment, half the male and half the female, weight 18 to 22 g. The mice were randomly divided into normal control group and three dosage groups of the composition of Example 1, including low dosage group, middle dosage group and high dosage group. There were 10 animals in each group. The mice were administered by intragastric gavage 0.2 ml/10 g body weight once per day and the administration lasted for 10 days. The normal control group was administered with equal volume of distilled water. 24 h after the last administration, the animals were sacrificed, and a suspension of spleen cells was prepared under aseptic conditions.

1) Preparation of the suspension of spleen cells: mice were sacrificed by cervical dislocation, the mice were immersed in 75% ethanol for about 1 min; the spleen was taken out on a super-clean bench and disposed in RPMI 1640 culture medium without serum. The spleen was homogenized to single cells with a 100-mesh stainless steel mesh and centrifuged at 1000 rpm for 5 min. The supernatant was discarded and the cell precipitation was gently knocked for loose. 0.4 mL of double distilled water was added to the cells and gently shaken for 30 s to break the red blood cells under low osmotic pressure. Then 0.4 mL of double-concentration physiological saline (1.8%) was added so that the solution recovered isosmotic. The cells suspension was subjected to centrifugation at 1000 rpm for 5 min, and washed twice with 1640 culture medium without serum.

The cell precipitation was re-suspended in 1640 culture medium containing 10/o of calf serum and counted under a microscope. The cell concentration was adjusted to $5\times10^6$/mL, i.e., the spleen cells for use.

2) Target cell: one day before the experiment, the medium of L929 cells was changed. In the experiment, 1 to 2 ml of 0.25% trypsin was used to digest the cells for 1 to 2 min. Complete 1640 medium was added, and the cells were gently blown so that the cells detached from the wall. The mixture was subjected to centrifugation at 1000 rpm for 5 min and the supernatant was discarded. The cell precipitation was re-suspended in 1640 medium containing 10% of calf serum. The cell concentration was adjusted to $1\times10^5$/mL, i.e., the target cells for use.

Test of NK cell activity: the target cell suspension was added respectively to a 96-well plastic culture plate in an amount of 0.1 mL/well. The plate was put into an incubator with 5% $CO_2$ at 37° C. for 4 h so that the target cells formed single-layer cells on the bottom. Then, 0.1 mL of effector cells obtained in step 1) were added to each well (effector cells:target cells=50:1). Each sample was performed in duplicate. For the control well, 0.1 mL of complete 1640 medium was added. The plate was put into an incubator with 5% $CO_2$ at 37° C. for 20 h. At the end of the experiment, the supernatants were discarded, and all the wells were gently filled with physiology saline for 3 times to remove the effector cells the target cells which were killed by the effector cells. Remaining liquid in the wells was dried by filter paper and 0.1 mL of 0.1% neutral red dye solution was added to each well. The plate was incubated at 37° C. for 30 min, and the dye solution was removed. After washing with physiology saline for three times, 0.1 mL of cell lysis solution (50% acetic acid and 50% ethanol) was added to each to each well to break the target cells which have neutral red, so that neutral red in the cells was released. The plate was gently shaken for mixing. The optical density was measured with an enzyme-linked analyzer at 492 nm, reference wavelength 450 nm, and the OD values were recorded. The formula is:

$$\text{Killing rate} = \frac{\text{OD value of the target cell} - \text{OD value of the experiment group}}{\text{OD value of the target cell}} \times 100$$

TABLE 5

Effects on the activity of NK cells ($\bar{x} \pm s$)

| Group | Dosage (ml/kg) | N (animal number) | Kill Rate(%) |
|---|---|---|---|
| Control Group | — | 10 | 2 26 ± 4.65 |
| Low Dosage Group | 1.67 | 10 | 1.95 ± 3.21 |
| Middle Dosage Group | 3.33 | 10 | 1.82 ± 3.07 |
| High Dosage Group | 6.67 | 10 | 8.55 ± 3.96* |

(Comment: comparing with the control group, * p<0.05, and ** p<0.01.)

The results of Table 5 showed that high dosage group of Example 1 significantly increased the activity of NK cells and improved the killing rate of NK cells (p<0.05).

5. Fatigue Resistance Test

SPF grade KM mice were used in the experiment, half the male and half the female, weight 18 to 22 g. The mice were randomly divided into normal control group and three dosage groups of the composition of Example 1, including low dosage group, middle dosage group and high dosage group. There were 10 animals in each group. The mice were administered by intragastric gavage once per day and the administration lasted for 7 days. The normal control group was administered with equal volume of distilled water. 30 min after the last administration, the mice were loaded with iron wire that was 10% of body weight, and put into water to swim (the water temperature was 25° C. and the depth was 20 cm). Observed until the mice were exhausted (stayed below water for 10 s without coming up), and the time was recorded as the swimming time. The results were recorded and subjected to statistical analysis. The results were shown in Table 6.

TABLE 6

Effects on mice swimming time ($\bar{x} \pm s$)

| Group | Dosage (ml/kg) | N (animal number) | Swimming Time (sec) |
|---|---|---|---|
| Normal Control Group | — | 10 | 118.67 ± 65.68 |
| Low Dosage Group | 1.67 | 10 | 161.11 ± 22.09* |
| Middle Dosage Group | 3.33 | 10 | 216.70 ± 94.51** |
| High Dosage Group | 6.67 | 10 | 162.00 ± 37.59* |

Results in Table 6 showed that low, middle and high dosage of composition in Example 1 obviously extended the swimming time of mouse (P<0.05 to 0.01), wherein the middle dosage extremely significantly extended the swimming time of mouse.

6. Test of Ameliorating Kidney-Yang Deficiency Syndrome

Male SPF grade SD rats were used, weight 180 to 220 g. The rats were randomly divided into normal control group, model control group, and three dosage groups of the composition of Example 1, including low dosage group, middle dosage group and high dosage group. There were 10 rats in the normal control group, and 13 rats in other groups. From the $1^{st}$ day of the experiment, except for the normal control group, rats in other groups were subcutaneous injected with tydrocortisone in an amount of 25 mg/kg body weight. The administration lasted for 14 days to establish the Kidney-Yang Deficiency Syndrome animal model. Meanwhile, the rats were administered with the composition by intragastric gavage every day, and the normal control group and the model control group were administered with equal volume of distilled water. On the $15^{th}$ day of the experiment, blood samples were collected from orbit of the animals. The serum was separated and subjected to different tests. T3, T4, T and Cor were measured by radioimmunoassay method. CRH, ACTH, TRH, TSH, GnRH, FSH and LH were measured by ELASA according to the instruction of the kit. The animals were sacrificed and hypophysis, thymus and thyroid gland were weighed, and the organ coefficients were calculated. The results were shown in tables 7 to 10.

$$\text{Organ coefficient} = \frac{\text{weight of organ (mg)}}{\text{body weight (g)}} \times 100\%$$

TABLE 7

Effects on organ coefficient of Kidney-Yang Deficiency Syndrome animals ($\bar{x} \pm s$)

| Group | Dosage ml/kg | Hypophysis | Thymus | Thyroid Gland |
|---|---|---|---|---|
| Normal Control Group | — | 0.031 ± 0.005 | 0.65 ± 0.24 | 0.53 ± 0.07 |
| Model control Group | — | 0.011 ± 0.006▲▲ | 0.23 ± 0.09▲▲ | 0.40 ± 0.07▲▲ |
| Low Dosage Group | 0.83 | 0.021 ± 0.010 | 0.25 ± 0.08 | 0.45 ± 0.15 |
| Middle Dosage Group | 1.67 | 0.017 ± 0.009 | 0.24 ± 0.10 | 0.49 ± 0.11* |
| High Dosage Group | 3.33 | 0.026 ± 0.011* | 0.35 ± 0.07* | 0.55 ± 0.15** |

Comment: ▲ indicating that comparing with the normal control group, P<0.05; ▲▲ indicating that comparing with the normal control group, P<0.01; * indicating that comparing with the normal control group, P<0.05; ** indicating that comparing with the normal control group, P<0.01.

Results of Table 7 showed that in the Kidney-Yang Deficiency Syndrome animal model, the thymus coefficient, hypophysis coefficient and thyroid gland coefficient obviously decreased (P<0.01). High dosage of the composition of Example 1 obviously increased the thymus coefficient, hypophysis coefficient and thyroid gland coefficient of the kidney yang deficient animal (P<0.05 to 0.01), and the middle dosage significantly increased the thyroid gland coefficient (P<0.05).

TABLE 8

Effects on function of hypothalamus-hypophysis-adrenal gland axis of Kidney-Yang Deficiency Syndrome animals ($\bar{x} \pm s$)

| Group | Dosage ml/kg | CRH pg/ml | ACTH pg/ml | COR nmol/L |
|---|---|---|---|---|
| Normal Control | — | 101.84 ± 24.70 | 222.47 ± 55.05 | 115.91 ± 23.27 |
| Model Control | — | 65.79 ± 22.58▲▲ | 144.40 ± 47.48▲ | 45.90 ± 22.96▲▲ |
| Low Dosage Group | 0.83 | 82.94 ± 22.26 | 198.68 ± 48.79 | 71.96 ± 25.09* |
| Middle Dosage Group | 1.67 | 71.30 ± 19.04 | 147.62 ± 56.55 | 75.96 ± 19.33* |
| High Dosage Group | 3.33 | 98.58 ± 20.82* | 157.38 ± 67.75 | 95.42 ± 12.31** |

Comment: ▲ indicating that comparing with the normal control group, P<0.05; ▲▲ indicating that comparing with the normal control group, P<0.01; * indicating that comparing with the normal control group, P<0.05; ** indicating that comparing with the normal control group, P<0.01.

Results of Table 8 showed that comparing with the normal control group, the corticotropin releasing hormone (CRH), adrenocorticotropic hormone (ACTH) and cortisol (Cor) level of the Kidney-Yang Deficiency Syndrome animal model group significantly decreased (P<0.05 to 0.01). The high dosage group of the composition of Example 1 significantly increased the serum CRH and COR levels in Kidney-Yang Deficiency Syndrome rats (P<0.05 to 0.01); and the low and middle dosage groups obviously increased COR level (P<0.05).

TABLE 9

Effects on function of hypothalamus-hypophysis-thyroid gland axis of Kidney-Yang Deficiency Syndrome animals ($\bar{x} \pm s$)

| Group | Dosage ml/kg | TRH ng/ml | TSH mIU/ml | T3 nmol/L | T4 nmol/L |
|---|---|---|---|---|---|
| Normal Control Group | — | 4.99 ± 0.0.33 | 0.428 ± 0.205 | 0.62 ± 0.13 | 25.5 ± 3.78 |
| Model Control Group | — | 4.50 ± 0.50▲ | 0.200 ± 0.094▲ | 0.48 ± 0.19▲ | 18.98 ± 4.88▲▲ |
| Low Dosage Group | 0.83 | 3.43 ± 1.06 | 0.284 ± 0.230 | 0.50 ± 0.17 | 22.79 ± 6.69 |
| Middle Dosage Group | 1.67 | 5.50 ± 2.10 | 0.287 ± 0.210 | 0.44 ± 0.07 | 19.58 ± 5.55 |
| High Dosage Group | 3.33 | 6.80 ± 0.73** | 0.222 ± 0.155 | 0.69 ± 0.22* | 27.54 ± 6.90* |

Comment: ▲ indicating that comparing with the normal control group, P<0.05; ▲▲ indicating that comparing with the normal control group, P<0.01; * indicating that comparing with the normal control group, P<0.05; ** indicating that comparing with the normal control group, P<0.01.

Results of Table 9 showed that comparing with the normal control group, the thyrotropin-releasing hormone (TRH), thyroid stimulating hormone (TSH), triiodothyronine (T3), and tetraiodothyronine (T4) levels in Kidney-Yang Deficiency Syndrome animal model were significantly decreased (P<0.05 to 0.01). Comparing with the model group, high dosage of the composition of Example 1 significantly increased the serum TRH, T3 and T4 levels in the Kidney-Yang Deficiency Syndrome rats (P<0.05 to 0.01).

TABLE 10

Effects on function of hypothalamus-pituitary-thyroid gland axis of Kidney-Yang Deficiency Syndrome animals ($\bar{x} \pm s$)

| Group | Dosage ml/kg | GnRH ng/ml | FSH mIU/ml | LH mIU/ml | T nmol/L |
|---|---|---|---|---|---|
| Normal Control Group | — | 8.08 ± 0.88 | 0.183 ± 0.038 | 1.185 ± 0.462 | 2.97 ± 1.41 |
| Model Control Group | — | 7.49 ± 1.34 | 0.149 ± 0.018▲ | 0.713 ± 0.063▲▲ | 1.57 ± 1.02▲ |
| Low Dosage Group | 0.83 | 7.90 ± 0.83 | 0.182 ± 0.038* | 0.959 ± 0.249 | 1.90 ± 0.58 |
| Middle Dosage Group | 1.67 | 7.99 ± 1.01 | 0.166 ± 0.026 | 0.843 ± 0.134 | 3.20 ± 2.02 |
| High Dosage Group | 3.33 | 10.51 ± 1.33 | 0.167 ± 0.017 | 0.761 ± 0.084 | 3.93 ± 2.89* |

Comment: ▲ indicating that comparing with the normal control group, P<0.05; ▲▲ indicating that comparing with the normal control group, P<0.01; * indicating that comparing with the normal control group, P<0.05; ** indicating that comparing with the normal control group, P<0.01.

The results of Table 10 showed that comparing with the normal control group, the follicle stimulating hormone (FSH), luteinizing hormone (LH), testosterone (T) levels of the Kidney-Yang Deficiency Syndrome animal group significantly decreased (P<0.05 to 0.01). Comparing with the model group, low dosage group of the composition in Example 1 significantly increased the FSH level in Kidney-Yang Deficiency Syndrome rats (P<0.05); and the high dosage group significantly increased T level (P<0.05).

Example 3: Evaluation Among the Crowd

1. Design of the Test

In the test, the composition of Example 1 was subjected to a consumer indwelling test to observed the effects of two compositions on male immunity/fatigue (poor immunity, dizziness, easy to be fatigue/weak, sleepiness and lack of concentration) and Kidney-Yang Deficiency Syndrome (waist and knees aching and limping, afraid of chill and cold, limbs chilling, frequent nocturia and loss of libido). Comparative analysis was carried on efficacy and satisfaction.

2. Samples

Male, aged from 30 to 60.

Each subject has at least one symptom of low immunity (poor immunity and dizziness), two symptoms of fatigue (easy to be fatigue/weak, sleepiness and lack of concentration) and three symptoms of Kidney-Yang Deficiency Syndrome (the symptoms appeared at least once or more every week).

The subjects have tried to ameliorate the body symptoms in a certain way, for example, diet/traditional Chinese medicine/cosmetology/healthcare products (had stopped in the last two weeks) and so on.

The symptoms under test were not due to a clear cause; and there was no medically diagnosed organic disease.

The subjects did not have long-term fixed medication (prescription and over-the-counter) history Location (city where the evaluation was carried out): Harbin and Changsha Time: one month Number of the completed samples: 213

3. Evaluation Standard

The efficacy was excellent and the subject was very satisfied: 5 points.

The efficacy was very good and the subject was relatively satisfied: 4 points.

The efficacy was expected and the subject was basically satisfied: 3 points.

There was certain efficacy and acceptable: 2 points.

There was little efficacy and the subject was not satisfied: 1 point.

4. Results

TABLE 11

| | Index of Observation | Average Onset Time (Day) | Satisfaction (1 to 5 Points) |
|---|---|---|---|
| Immunity/ Fatigue | Poor Immunity | 15.37 | 3.12 |
| | Dizziness | 17.43 | 3.02 |
| | Easy to be Fatigue/Weak | 15.30 | 3.27 |
| | Sleepiness | 15.78 | 3.05 |
| | Lack of Concentration | 16.21 | 2.95 |
| Kidney-Yang Deficiency Syndrome | Waist and Knees Aching and Limping | 15.93 | 3.24 |
| | Afraid of Chill and Cold | 17.96 | 2.89 |
| | Limbs Chilling | 18.47 | 3.02 |
| | Frequent Nocturia | 15.40 | 3.14 |
| | Loss of Libido | 21.95 | 2.73 |

Results in Table 11 showed that the composition of the present disclosure can achieve an effect in a relatively short time, which was about 15 days, and the subjects were generally satisfied with the efficacy achieved by the composition.

The above description is only a preferred embodiment of the present disclosure. It should be noted that a number of modifications and refinements may be made by one of ordinary skill in the art without departing from the principles of the present disclosure, and such modifications and modifications are also considered to be within the protection scope of the disclosure.

What is claimed is:

1. A method for producing a composition having functions of improving kidney yang, enhancing immunity, and relieving fatigue, comprising:

mixing Astragali radix, Rehmanniae radix, Eucommiae cortex, Morindae Officinalis radix, Lycii fructus, and Polygonati radix, adding distilled water 12 times the weight of starting materials, boiling and extracting for 90 min, and collecting the filtrate upon filtration; adding distilled water 10 times the weight of filter cake, boiling and extracting for 60 min, and collecting the filtrate upon filtration; combining the two filtrates, and subjecting the resultant filtrate to 80-mesh filtration; performing vacuum concentration under condition of −0.05 MPa at 70° C. to obtain the extractum, adding purified water and a sweetener to the extractum, mixing under stirring for 30 min, centrifuging to remove precipitations, and sterilizing at a high temperature to obtain the composition.

* * * * *